United States Patent [19]

Keitzman

[11] Patent Number: 4,856,511
[45] Date of Patent: Aug. 15, 1989

[54] SURGICAL INSTRUMENT FOR INTRAOCULAR LENS IMPLANTATION

[76] Inventor: Benjamin Keitzman, 0N620 Indian Knoll Rd., West Chicago, Ill. 60185

[21] Appl. No.: 299,355

[22] Filed: Jan. 23, 1989

[51] Int. Cl.⁴ .......................... A61B 17/00; A61F 2/16
[52] U.S. Cl. ............................................... 128/303 R
[58] Field of Search ............ 623/6; 128/303 R, 334 R

[56] References Cited

U.S. PATENT DOCUMENTS

| | | | |
|---|---|---|---|
| 4,530,117 | 7/1985 | Kelman | 128/303 R X |
| 4,536,896 | 8/1985 | Bittner | 623/6 |
| 4,579,116 | 4/1986 | Catalano | 128/303 R |
| 4,681,101 | 7/1987 | Bicoll | 128/303 R |
| 4,702,244 | 10/1987 | Mazzocco | 128/303 R |
| 4,726,367 | 2/1988 | Shoemaker | 128/303 R |
| 4,773,415 | 9/1988 | Tan | 128/303 R |

*Primary Examiner*—Ronald L. Frinks
*Attorney, Agent, or Firm*—Allegretti & Witcoff, Ltd.

[57] ABSTRACT

An instrument (10) for accurately guiding a superior lens haptic (20) into the capsular bag to insure that both the inferior haptic (21) and superior haptic (20) are positioned within the confines of the capsular bag to effect lens centration. The instrument (10) comprises a stainless steel wire shaft (12) having a loop (16) on one end and a handle (14) on the other end. The wire has a diameter of 0.022 in. and the loop has an internal diameter of 0.6 mm and the orientation of the loop is critical. The shaft is bent at a point where it connects to the loop so that the loop, when observed from the handle, is inclined at an angle of 45 degrees to the right from the axis of the shaft and the side of the loop facing the observer is tilted downwardly from the axis of the shaft to an angle of about 45 degrees. Thus, the loop is inclined laterally and downwardly and when held in the left hand, placed inside the eye with the loop slid over the base of the superior lens haptic, the angulation of the loop points the lens haptic directly toward the equator of the capsular bag.

3 Claims, 1 Drawing Sheet

SURGICAL INSTRUMENT FOR INTRAOCULAR LENS IMPLANTATION

This invention relates to a surgical instrument for inserting an intraocular lens into the capsular bag of the eye.

PRIOR ART

After an extracapsular cataract extraction, the ophthalmic surgeon places a posterior chamber intraocular lens within the capsular bag. The intraocular lens is made of plastic for example, polymethylmethacrylate and has two haptic loops connected thereto consisting of a flexible nylon, acrylic or similar polymer filament to facilitate manipulation and fixation of the lens. The success of the placement depends in large part on the surgeon's manual dexterity as he compresses and manipulates the superior haptic to clear the capsule margin and release it toward what he hopes is the secure confines of the capsular bag. This maneuver is accomplished using forceps for holding and manipulating the haptic Most of the time, the maneuver succeeds, but many times it does not, leaving one loop in the bag and one loop in the sulcus. The capsular bag is covered by the iris and cannot be seen and this makes the placement difficult.

In 425 postmortem studies conducted at Center for Intraocular Lens Research, Medical University of South Carolina, researchers found asymmetric fixation in 53% of the eyes, resulting in a mean decentration of almost 1 mm. Fixation of both haptics in the bag appeared in 30% of the eyes and fixation of both haptics in the ciliary sulcus accounted for 18%. Off center placement results in shifting or decentering of the lens to cause glare or imbalance between the eyes. Misplacement of the haptic in areas outside the capsular bag can cause erosion and hemorrhaging due to pressure from the haptic.

THE INVENTION

The objective of the invention is to provide an instrument for accurately guiding the lens haptic into the capsular bag. The instrument comprises a stainless steel wire shaft having a loop on one end and a handle on the other. The wire has a diameter of 0.022 in. and the loop formed at the end thereof has an internal diameter of 0.6 mm. The orientation of the loop is critical. The shaft is bent at a point where it connects to the loop so that the loop, when observed from the handle, is inclined at an angle of 45 degrees to the right from the axis of the shaft. Furthermore, the side of the loop facing the observer is tilted downwardly from the axis of the shaft to an angle of about 45 degrees. Thus, the loop is inclined laterally and downwardly. When held in the left hand and placed inside the eye over the base of the superior lens haptic, the angulation of the loop points the lens haptic directly toward the equator of the capsular bag.

In placing an intraocular lens into the capsular bag, the inferior haptic of the lens is inserted into the capsular bag inferiorly. The superior haptic is threaded through the eye of the instrument held in the left hand. The loop of the instrument is moved along the haptic to the point where the haptic joins the lens, a position near the pupillary margin where one can see clearly that the base of the haptic is behind the capsular margin. The lens is then dialed from vertical to horizontal orientation by engaging the crotch of the haptic with a hook such as a modified Lester hook. As the dialing occurs, the haptic enters the capsular bag smoothly and atraumatically by sliding through the eye of the loop of the instrument. Very little, if any, manipulation is required thereafter to refine the centration of the lens. The instrument may be used for guiding various types of C-loop lenses into the capsular bag.

Because the invention permits accurately placing the intraocular lens in the capsular bag, the lens is held securely by the bag including the superior haptic loop attached to the lens. No suturing of the bag is necessary.

DETAILED DESCRIPTION

Figure 5:
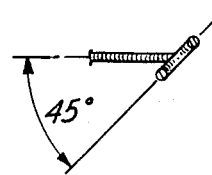
FIG. 5 is a sectional view along the line 5,5 of FIG. 3.

Referring to FIGS. 2-5, instrument 10 has a shank 12, a knurled handle 14 and a loop 16 with an eye 18. The shank is made from stainless steel wire 0.022 in. in diameter. The loop 16 at the outer end of the shank is bent 45 degrees laterally from the axis of the shaft. When viewed from the handle, the inclination of the loop is to the right. From this first position, the side of the bent loop facing the observer is bent downwardly 45 degrees from the axis of the shank or from the plane of the loop in this first position, as shown in FIG. 5. The eye 18 of the loop has a diameter of 0.6 mm. just large enough to permit the haptic to slide freely therethrough. All surfaces of the loop are polished and smooth.

Figure 1:
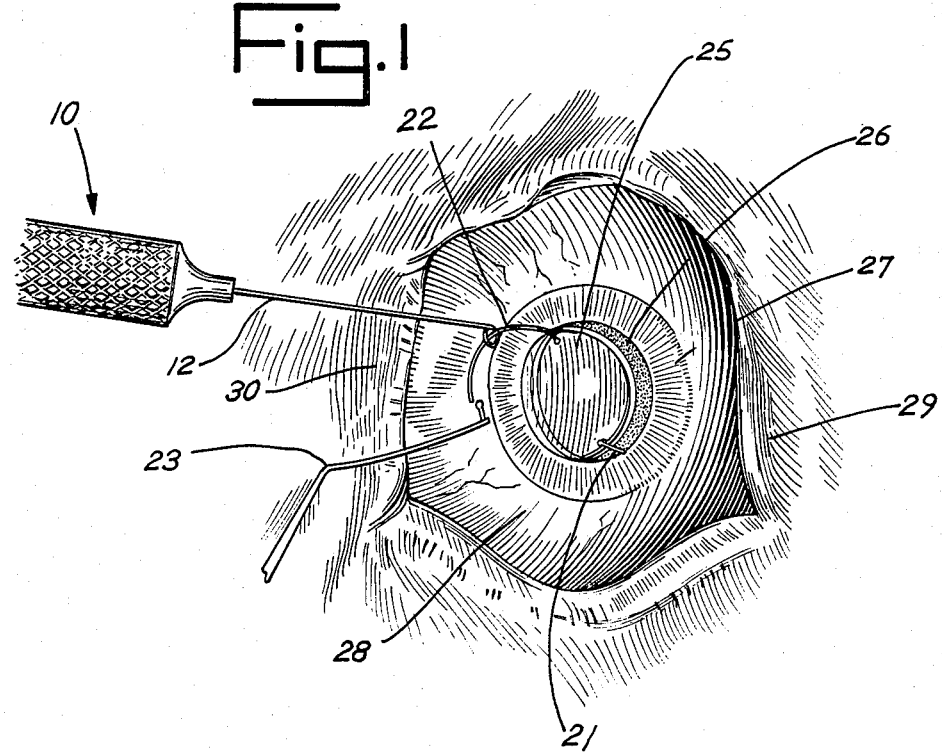
FIG. 1 is a front elevation view of an eye showing the instrument of the invention guiding a lens into position in the capsular bag.
Figure 2:
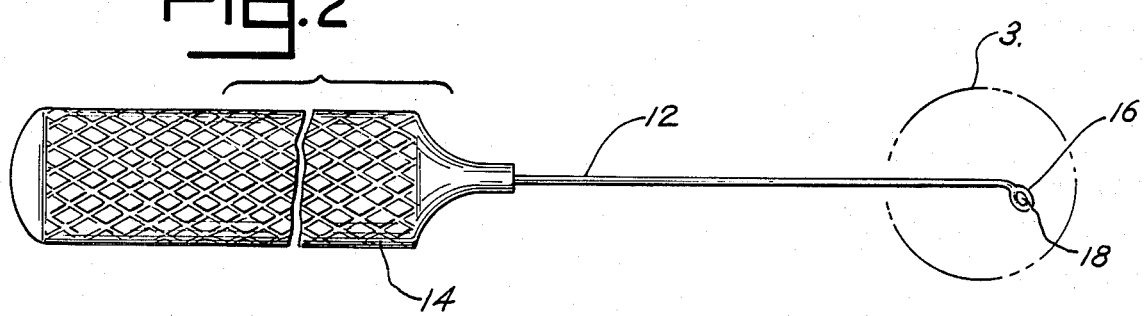
FIG. 2 is a side view of the instrument constructed in accordance with the invention.
Figure 3:
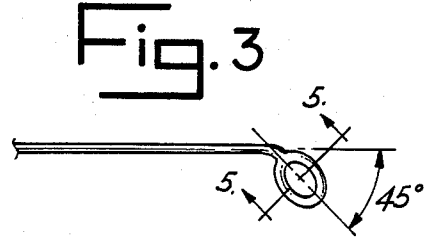
FIG. 3 is an enlarged view of the loop end of the instrument.
Figure 4:
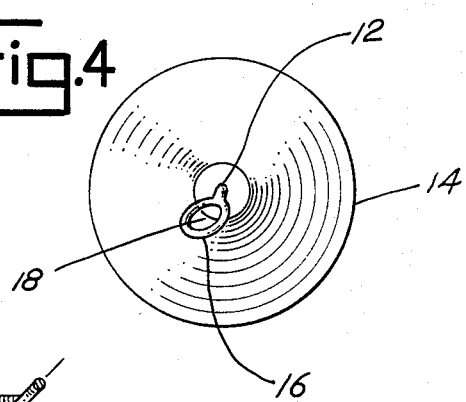
FIG. 4 is an end view of the instrument from the loop end.

Referring to FIG. 1, the procedure for using the instrument to implant a lens in the capsular bag will be described. The portions of the eye shown in the drawing are: dilated pupil 26, cornea 27, sclera 28, lower eye lid margin 29, upper eye lid margin 30. The plastic lens 25 has an inferior lens haptic 21 and a diametrically opposite superior haptic loop 22 connected thereto. In FIG. 1, the inferior lens haptic is shown entering the capsular bag inferiorly, while the top of the lens is still outside the capsular bag.

The eye is sutured (sutures not shown) to hold the eye in a steady position during insertion of the intraocular lens. The instrument 10 is held in the surgeon's left hand. The superior haptic loop 22 is threaded through the eye 18 of loop 16. The angular orientation of loop 16 facilitates the manipulation of the haptic loop 22 to ease the lens 25 into the capsular bag beneath the cornea and iris. In the surgeon's right hand is a modified Lester hook, the end of which is designated by the numeral 23. In FIG. 1, the hook is poised to engage the edge of lens 25 and dial it from the vertical to a horizontal orientation.

I claim:

1. A surgical instrument for inserting an intraocular lens implant into the lens capsule of an eye comprising
    a wire terminating in a loop;
    a handle connecting to the end of the wire opposite said loop;

said loop, when observed from the handle, being bent toward the observer about 45 degrees to the right from the axis of said wire to a first position; and further having the side of the bent loop facing the observer tilted downwardly about 45 degrees from the axis of the wire.

2. The instrument of claim 1 in which said wire is made from stainless steel, has a diameter of 0.022 in. and the eye formed by the loop has a diameter of 0.6 mm.

3. The instrument of claim 2 in which said wire is polished to provide a smooth surfaced loop.

* * * * *

UNITED STATES PATENT AND TRADEMARK OFFICE
CERTIFICATE OF CORRECTION

PATENT NO. : 4,856,511

DATED : August 15, 1989

INVENTOR(S) : Benjamin Kietzman

It is certified that error appears in the above-identified patent and that said Letters Patent is hereby corrected as shown below:

Title page item (19) "Keitzman" should read--Kietzman--.

Item (76) inventor; should read--Benjamin Kietzman--.

Signed and Sealed this

Seventh Day of January, 1992

Attest:

HARRY F. MANBECK, JR.

*Attesting Officer*      *Commissioner of Patents and Trademarks*